United States Patent [19]

Saito et al.

[11] Patent Number: 4,804,673
[45] Date of Patent: Feb. 14, 1989

[54] FUNGICIDAL SULFONYL AZOLES

[75] Inventors: Junichi Saito, Mitaka; Tatsuo Tamura, Hamura; Yoshio Kurahashi; Noboru Matsumoto, both of Hachioji; Naoko Yamaguchi, Hino, all of Japan

[73] Assignee: Nihon Tokushu Noyaku Seizo K.K., Tokyo, Japan

[21] Appl. No.: 25,298

[22] Filed: Mar. 12, 1987

[30] Foreign Application Priority Data

Mar. 20, 1986 [JP] Japan .................. 61-60642

[51] Int. Cl.$^4$ .................. A01N 43/50; C07D 233/56; C07D 233/68
[52] U.S. Cl. .................. 514/398; 514/397; 548/336; 548/337; 548/338; 548/340
[58] Field of Search .............. 548/337, 336, 338, 340; 514/397, 398

[56] References Cited

U.S. PATENT DOCUMENTS 4,115,060  9/1978  Finley et al. .................. 8/111

FOREIGN PATENT DOCUMENTS 0044394  1/1982  European Pat. Off. ............ 548/337
0091794  10/1983 European Pat. Off. ............ 548/306
0173918  3/1986  European Pat. Off. ............ 548/337

OTHER PUBLICATIONS

*Chemical Abstracts,* 93:95560q (1980), [Ogilvie, K., et al., *Nucleic Acids Res.,* 1980, 8(9), 2105–15].
*Chemical Abstracts,* 97:216195t (1982), [Jpn. Kokai Tokyo Koho JP 82 116 067, Jul. 19, 1982].
*Chemical Abstracts,* 97:162986f (1982), [Jpn. Kokai Tokyo Koho JP 82 120 574, Jul. 27, 1982].

*Primary Examiner*—Richard A. Schwartz
*Attorney, Agent, or Firm*—Sprung Horn Kramer & Woods

[57] ABSTRACT

Fungicidally active sulfonyl azoles of the formula

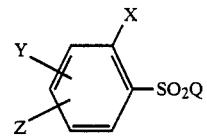

in which
X represents hydrogen, alkyl, halogen, alkoxy or aryl,
Y represents hydrogen, alkyl, halogen, nitro or alkoxy,
Z represents hydrogen, alkyl, halogen or alkoxy, or
Y and Z may together represent an optionally substituted cyclic ring which can contain hetero atoms and
Q represents a radical of the formula

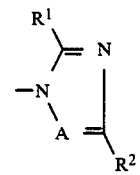

in which
A represents a $-N=$ radical or a

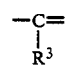

radical,
$R^1$ represents hydrogen, alkyl or aryl, and
$R^2$ and $R^3$ each represent hydrogen, alkyl, halogen or nitro with the proviso that $R^1$, $R^2$ and $R^3$ may all simultaneously be hydrogen only if Y and Z together represent an optionally substituted ring, or
Q represents 1H-benzotriazol-1-yl radical or 1H-tetrazol-1-yl radical.

9 Claims, No Drawings

FUNGICIDAL SULFONYL AZOLES

The present invention relates to novel sulfonyl azoles, to a process for their preparation, and to their use as fungicides in agriculture and horticulture.

It has already been disclosed that certain sulfonyl azoles are useful as a bleaching agent (see Japanese patent laid-open No. 64181/1979) corresponding to U.S. Pat. No. 4,115,060 and as agricultural fungicide (see Japanese patent laid-open No. 28053/1982).

It has now been found that the sulfonyl azoles of the formula (I)

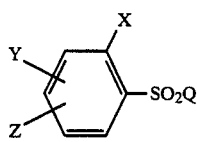
(I)

in which
X represents hydrogen, alkyl, halogen, alkoxy or aryl,
Y represents hydrogen, alkyl, halogen, nitro or alkoxy,
Z represents hydrogen, alkyl, halogen or alkoxy, or
Y and Z may together represent an optionally substituted cyclic ring which can contain hetero atoms, for example, oxygen,
Q represents a radical of the formula

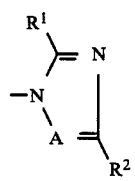

in which
A represents a —N= radical or a

radical,
wherein
$R^1$ represents hydrogen, alkyl or aryl, and
$R^2$ and $R^3$ each represent hydrogen, alkyl, halogen or nitro with the proviso that $R^1$, $R^2$ and $R^3$ may all simultaneously be hydrogen only if Y and Z together represent an optionally substituted ring, or
Q represents 1H-benzotriazol-1-yl radical or 1H-tetrazol-1-yl radical.

The compounds of the formula (I) can be produced by a general process, wherein a compound of the formula (II)

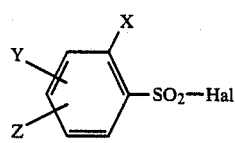
(II)

in which X, Y and Z have the meanings mentioned above, and Hal represents halogen, is reacted with a compound of the formula (III)

M—Q (III)

in which
Q has the meaning mentioned above, and
M represents hydrogen, an alkali metal or an alkaline earth metal equivalent,
in the presence of an inert solvent and if appropriate, in the presence of a base.

The novel sulfonyl azoles of the formula (I) exhibit a powerful action as agricultural and horticultural fungicides, and have a broad spectrum of action, while they do not damage crop plants. Particularly, the active compounds (I) exhibit a very high fungicidal action against late blight of tomato plants and the like.

In the formula (I) of the compounds according to the invention,
X preferably represents alkyl with 1 to 4 carbon atoms,
Y preferably represents fluorine, chlorine, bromine, nitro or alkyl with 1 to 4 carbon atoms,
Z preferably represents hydrogen and
Q preferably represents a radical of the formula

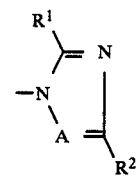

in which
A represents

radical,
$R^1$ represents hydrogen or alkyl with 1 to 4 carbon atoms, and
$R^2$ and $R^3$ each represent hydrogen or halogen with the proviso that not all R-substituents are hydrogen at the same time, or
Q represents 1H-benzotriazol-1-yl radical or 1H-tetrazol-1-yl radical.

More preferably,
X of the formula (I) represents methyl,
Y represents chlorine, bromine, nitro or alkyl with 1 to 3 carbon atoms,
Z represents hydrogen, and
Q represents a 2-methylimidazol-1-yl radical, 4,5-dichloroimidazol-1-yl radical, a 1H-benzotriazol-1-yl radical or 1H-tetrazol-1-yl radical.

Examples of compounds of the formula (I) according to the invention are:
1-(2-chloro-6-methyl-benzene-sulfonyl)-2-methyl-imidazole,
1-(2,5-dimethyl-benzene-sulfonyl)-1H-tetrazole,
1-(2-methyl-5-nitro-benzene-sulfonyl)-4,5-dichloroimidazole, and
1-(5-chloro-2-methyl-benzene-sulfonyl)-1H-benzotriazole.

In the process for producing the present compounds of the formula (I), if 2-methyl-5-nitro-benzene-sulfonyl chloride and 4,5-dichloroimidazole are used as starting materials, the course of the reaction can be represented by the following equation:

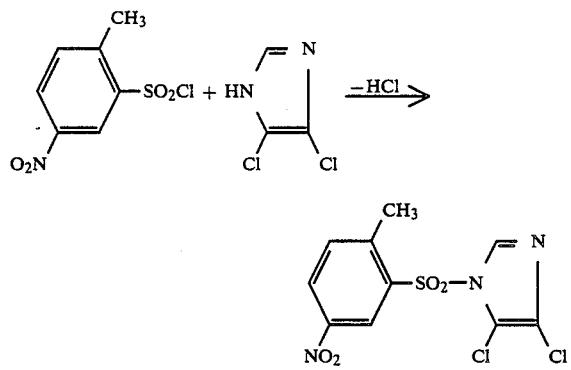

In the formula (II) of the starting compounds X, Y, Z and Hal have the same meanings as in the case of the formula (I) of the compounds to be produced. Furthermore, the preferred meanings of X, Y and Z of the formula (II) are the same as those shown in the case of the formula (I), Hal preferably represents chlorine.

The compounds of the formula (II) are generally well known compounds of organic chemistry. Examples of the compounds (II) are:
2,5-dimethyl-benzene-sulfonyl chloride,
2,6-dimethyl-benzene-sulfonyl chloride,
5-chloro-2-methyl-benzene-sulfonyl chloride,
5-bromo-2-methyl-benzene-sulfonyl chloride,
2-chloro-6-methyl-benzene-sulfonyl chloride,
2-methyl-5-nitro-benzene-sulfonyl chloride,
4-bromo-2-methyl-benzene-sulfonyl chloride, and
2-chloro-5-tert-butyl-benzene-sulfonyl chloride.

In the formula (III) of the compounds Q and M have the same meanings as those shown in the preceding paragraphs. The preferred meaning of Q is the same as that shown in the case of the formula (I), M preferably represents hydrogen or a sodium equivalent.

The compounds of the formula (III) are generally well known compounds in organic chemistry. Examples of the compounds (III) are imidazole, 2-methyl-imidazole, 2-ethyl-imidazole, 4-methyl-imidazole, 4,5-dichloro-imidazole, 1H-tetrazole, 1H-benzotriazole and the like.

As for 4,5-dichloro-imidazole shown above, it can be produced according to a known process disclosed in U.S. Pat. No. 3,409,606.

Preferred diluents for the process for the production of the compounds of the formula (I) are inert organic solvents. Examples of the solvent are water; aliphatic, cycloaliphatic or aromatic hydrocarbons and chlorinated hydrocarbons such as hexane, cyclohexane, petroleum ether, ligroin, benzene, toluene, xylene, methylene chloride, chloroform, carbon tetrachloride, ethylene chloride, trichloroethylene, chlorobenzene; ethers such as diethyl ether, methyl ethyl ether, diiso-propyl ether, dibutyl ether, propylene oxide, dioxane, tetrahydrofuran; ketones such as acetone, methyl ethyl ketone, methyl iso-propyl ketone, methyl iso-butyl ketone; nitriles such as acetonitrile propionitrile, acrylonitrile; alcohols such as methanol, ethanol, iso-propanol, butanol, ethylene glycol; esters such as ethyl acetate, amyl acetate; acid amides such as dimethyl formamide, dimethyl acetamide; sulfones and sulfoxides such as dimethyl sulfoxide, sulfolane; bases such as pyridine.

The reaction according to the invention may be carried out in the presence of an acid-binding agent. Examples of the acid-binding agents are conventional alkali metal hydroxides, carbonates, bicarbonates and alcoholates, and tertiary amines such as triethylamine, diethylaniline, pyridine, etc.

The reaction temperature in the process according to the invention may be varied within a wide range. For example, the process can be conducted at a temperature of from about −20° C. to the boiling point of the reaction mixture, preferably a temperature of about 0° to 100° C.

Although the reaction according to the invention is advantageously carried out under normal pressure, it may be also effected under a high pressure or a reduced pressure.

In carrying out the process according to the invention, the compounds of the formula (III) can be employed in an amount of about 1 to 2 moles per mole of the compounds of the formula (II) in the presence of a base such as pyridine in order to produce the desired compounds of the formula (I).

The active compounds according to the invention exhibit a powerful microbicidal action and can be employed in practice for combating undesired microorganisms. The active compounds are suitable for use as plant protection agents.

Fungicidal agents in plant protection, for example, are employed for combating Plasmodiophoromycetes, Oomycetes, Chytridiomycetes, Zygomycetes, Ascomycetes, Basidiomycetes and Deuteromycetes.

Bactericidal agents are employed in plant protection, for example, for combating Pseudomonoadaceae, Rhizobiaceae, Enterobacteriaceae, Corynebacteriaceae and Streptomycetaceae.

Some causative organisms of fungal and bacterial diseases included under the abovementioned main headings, are mentioned below as non-limiting examples: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonsopora species, such as, for example, *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. Graminea* (Conidial form: Drechslera, Synonym: Helminthosporium); Cochliobolus species, such as, for example, *Cochliobolus sativus* (Conodial form: Drechslera, Synonym: Helminthosporium); Uromyces species, such as, for example, *Uromyces appendicalatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example,

*Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

Especially, according to the invention, in addition to the aforesaid late blight of tomato (*Phytophthora infestans*), rice blast (*Pyricularia oryzae*), downy mildew on cucumber, melon and the like (*Pseudoperonospora cubensis*) and downy mildew on grape (*Prasmopara viticola*) may be cited as examples of the plant diseases.

The active compounds can be converted into the customary formulations, such as solutions, emulsions, suspensions, powders, foams, pastes, granules, aerosols, natural an synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for exampe by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

it is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving solid structure.

The active compounds can be used as such in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, f 0.00001 to 0.1% by weight, especially of 0.0001 to 0.02%, are generally employed.

The invention will be illustrated in more detail by way of the examples. However, it should be noted that the scope of the invention is not limited to the examples.

PREPARATIVE EXAMPLES

Example 1

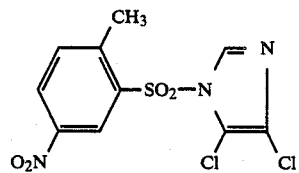

(Compound No. 22)

2.36 g of 2-methyl-5-nitro-benzene-sulfonyl chloride and 2.74 g of 4,5-dichloro-imidazole are dissolved in 20 ml of pyridine, and the resulting solution is stirred at 50° C. for 2 hours. The reaction solution is poured into 100 ml of ice water. The product, which crystallized out, is washed with a small amount of diethyl ether. 1.2 g of 1-(2-methyl-5-nitro-benzenesulfonyl)-4,5-dichloroimidazole, having a melting point of 125° to 130° C., are obtained.

EXAMPLE 2

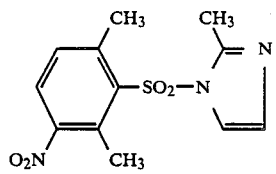

(Compound No. 15)

2.5 g of 2,6-dimethyl-3-nitro-benzene-sulfonyl chloride and 1.64 g of 2-methyl imidazole are dissolved in 20 ml of pyridine, and the resulting solution is stirred at 50° C. for 2 hours. The reaction solution is poured into 100 ml of ice water to crystallize out the product. The crystalline product thus obtained is washed with a small amount of diethyl ether. 1.5 g of 1-(2,6-dimethyl-3-nitro-benzene-sulfonyl)-2-methyl-imidazole, having a melting point of 99° to 101° C., are obtained.

The 2,6-dimethyl-3-nitro-benzene-sulfonyl chloride, which is employed as the starting material in Example 2, was prepared according to a known method described in "Helv. Chim. Acta", Vol. 61, No. 8, pages 3079 to 3086.

The compounds of the formula (I) which can be obtained in the same way as the above examples are shown in the following table together with Examples 1 and 2.

TABLE

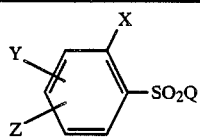

| Compound No. | X, Y, Z | Q | Physical constant |
|---|---|---|---|
| 1 | 2- | <br>CH₃<br>on imidazole | mp. 77–79° C. |
| 2 | 2,5-(CH₃)₂ | " | mp. 58–60° C. |
| 3 | 2,6-(CH₃)₂ | " | |
| 4 | 2,4,5-(CH₃)₃ | " | |
| 5 | 2-CH₃, 5-Cl | " | $n_D^{20}$ 1.5795 |
| 6 | 2-Cl, 6-CH₃ | " | mp. 143–146° C. |
| 7 | 2-CH₃, 5-Br | " | $n_D^{50}$ 1.5855 |
| 8 | 2-Cl, 5-tert.-C₄H₉ | " | |
| 9 | 2-OCH₃, 5-NO₂ | " | |
| 10 | 3,4-(OCH₃)₂ | " | mp. 92–94° C. |
| 11 | 3-O—CH₂—O—4 | " | |
| 12 | 2,5-Cl₂ | " | |
| 13 | 2,5-Br₂ | " | mp. 114–119° C. |
| 14 | 2,4,5-Cl₃ | " | |
| 15 | 2,6-(CH₃)₂, 3-NO₂ | " | mp. 99–101° C. |
| 16 | 2-CH₃, 5-Cl | C₂H₅ imidazole | |
| 17 | 2-CH₃, 5-Br | " | |

TABLE-continued

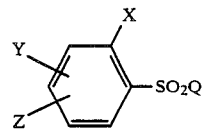

| Compound No. | X, Y, Z | Q | Physical constant |
|---|---|---|---|
| 18 | 2-CH₃, 5-NO₂ | 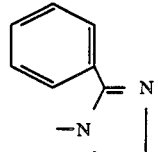 | mp. 145–150° C. |
| 19 | 2-CH₃, 5-NO₂ | 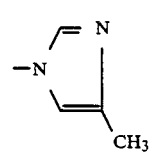 | mp. 111–115° C. |
| 20 | 2-CH₃, 5-NO₂ | 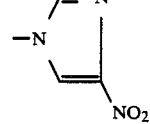 | mp. 150–155° C. |
| 21 | 2-CH₃, 5-NO₂ | 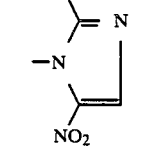 | mp. 180–190° C. |
| 22 | 2-CH₃, 5-NO₂ | 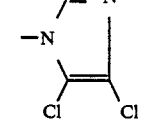 | mp. 125–130° C. |
| 23 | 2-CH₃, 5-Br | 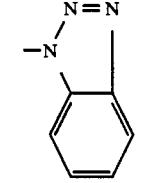 | mp. 121–127° C. |
| 24 | 2-Cl, 6-CH₃ | " | mp. 120–122.5° C. |
| 25 | 2-CH₃, 5-Cl | " | mp. 112–117° C. |
| 26 | 2-OCH₃, 5-Br | " | mp. 167–170° C. |
| 27 | 2,5-(CH₃)₂ | 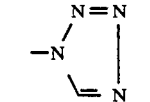 | mp. 111–116° C. |
| 28 | 2-CH₃, 5-NO₂ | " | |

TABLE-continued $$\begin{array}{c} X \\ Y \diagup \diagdown \\ | \quad | -SO_2Q \\ Z \diagdown \diagup \end{array}$$

| Compound No. | X, Y, Z | Q | Physical constant |
|---|---|---|---|
| 29 | (naphthalen-1-yl) | -SO₂-N(imidazole) | mp. 116-119° C. |
| 30 | (naphthalen-1-yl) | -SO₂-N(2-methylimidazole) | |
| 31 | 2-CH₃, 4-Br | -N(2-methylimidazole) | |

Use Example

Comparative compound A-1

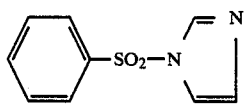

known from Japanese patent application disclosure No. 64181-1979;

Comparative compound A-2

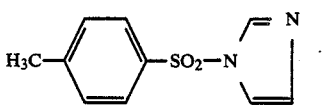

known from Japanese patent application disclosure No. 64181-1979;

Comparative compound C-1

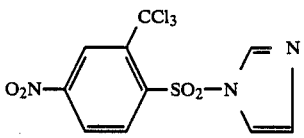

known from Japanese patent application disclosure No. 28053-1982.

EXAMPLE A

Late blight treatment test of tomato plants

Tomato plants (Kurihara Variety), which were grown in porcelain pots having a diameter of 9 cm, were treated by spraying an emulsion of an active compound with a spray gun to the plants.

One day after the spraying, the plants were inoculated with an aqueous spore suspension of the late blight causative organism. The plants were kept in an air-conditioned room at a constant temperature of 22° C. and a relative humidity of at least 90% over one night.

After 5 days, the infection of the plants was determined by measuring the area of the occurrence of lesion of the plants and by evaluating the degree of infection according to the following evaluation scale.

| Degree of infection | Area of occurrence of lesion on plant (%, based on whole area of plant) |
|---|---|
| 0 | 0 |
| 0.5 | up to 2 |
| 1 | 3-5 |
| 2 | 6-15 |
| 3 | 16-30 |
| 4 | 31-50 |
| 5 | 51 or more |

$$\text{Degree of protection (\%)} = \frac{\left[\begin{array}{c}\text{Degree of infection} \\ \text{in untreated plant} \\ \text{group}\end{array}\right] - \left[\begin{array}{c}\text{Degree of infection} \\ \text{in treated plant} \\ \text{group}\end{array}\right]}{\left[\begin{array}{c}\text{Degree of infection} \\ \text{in untreated plant group}\end{array}\right]} \times 100$$

The results of the tests, wherein a number of the present active compounds were employed, are shown in Table A.

TABLE A

| | Concentration of active compound (ppm) | Degree of protection (%) |
|---|---|---|
| Active compound No. | | |
| 6 | 500 | 100 |
| 19 | " | 100 |
| 22 | " | 100 |
| 25 | " | 100 |
| 27 | " | 100 |
| 29 | " | 100 |
| Comparative compound: | | |
| A-1 | 500 | 40 |
| A-2 | " | 50 |
| C-1 | " | 20 |

It will be understood that the specification and examples are illustrative but not limitative of the present invention and that other embodiments within the spirit and scope of the invention will suggest themselves to those skilled in the art.

We claim:

1. A compound selected from the group consisting of 1-(2-chloro-6-methyl-benzene-sulfonyl)-2-methyl imidazole and
1-(2-methyl-5-nitro-benzene-sulfonyl)-4,5-dichloroimidazole.

2. A compound according to claim 1, wherein such compound is 1-(2-chloro-6-methyl-benzene-sulfonyl)-2-methyl-imidazole of the formula

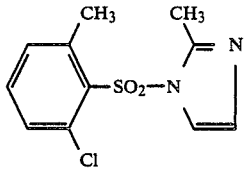

3. A compound according to claim 1, wherein such compound is 1-(2-methyl-5-nitro-benzene-sulfonyl)-4,5-dichloroimidazole of the formula

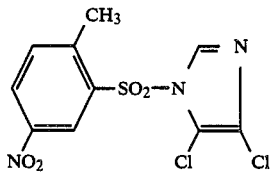

4. A fungicidal composition comprising a fungicidally effective amount of a compound according to claim 1 and a diluent.

5. A method of combating fungi which comprises applying to such fungi or to a fungus habitat a fungicidally effective amount of a compound according to claim 1 and a diluent.

6. A sulfonyl azole of the formula

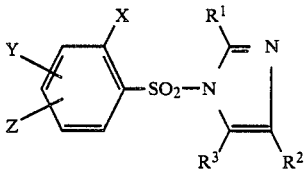

in which
X represents halogen, alkoxy with 1 to 4 carbon atoms or phenyl,
Y represents hydrogen, alkyl with 1 to 4 carbon atoms, halogen or alkoxy with 1 to 4 carbon atoms,
Z represents hydrogen, alkyl with 1 to 4 carbon atoms, halogen or alkoxy with 1 to 4 carbon atoms, or
Y and Z may together represent a cyclic ring which can contain oxygen atoms,
$R^1$ represents hydrogen, alkyl with 1 to 4 carbon atoms or phenyl,
$R^2$ represents hydrogen, alkyl with 1 to 4 carbon atoms, halogen or nitro, and
$R^3$ represents hydrogen, alkyl with 1 to 4 carbon atoms , halogen or nitro with the proviso that $R^1$, $R^2$ and $R^3$ may all simultaneously be hydrogen only if Y and Z together form a ring.

7. A sulfonyl azole according to claim 24, in which
Y represents fluorine, chlorine, bromine or alkyl with 1 to 4 carbon atoms,
Z represents hydrogen,
$R^1$ represents hydrogen or alkyl with 1 to 4 carbon atoms, and
$R^2$ represents hydrogen or halogen, and
$R^3$ represents hydrogen.

8. A fungicidal composition comprising a fungicidally effective amount of a compound according to claim 6 and a a diluent.

9. A method of combating fungi which comprises applying to such fungi or to a fungus habitat a fungicidally effective amount of a compound according to claim 6 and a diluent.

* * * * *